(12) United States Patent
White

(10) Patent No.: US 10,758,156 B2
(45) Date of Patent: Sep. 1, 2020

(54) MONITOR OF ORAL RESPIRATION

(71) Applicant: Child Mind Institute, Inc., New York, NY (US)

(72) Inventor: Curtis P. White, Queens, NY (US)

(73) Assignee: Child Mind Institute, Inc., New York, NY (US)

( * ) Notice: Subject to any disclaimer, the term of this patent is extended or adjusted under 35 U.S.C. 154(b) by 0 days.

(21) Appl. No.: 16/284,388

(22) Filed: Feb. 25, 2019

(65) Prior Publication Data

US 2019/0261889 A1 Aug. 29, 2019

Related U.S. Application Data

(60) Provisional application No. 62/634,775, filed on Feb. 23, 2018.

(51) Int. Cl.
*A61B 5/087* (2006.01)
*A61B 5/08* (2006.01)
*A61B 5/01* (2006.01)
*A61B 5/113* (2006.01)
*A61B 5/00* (2006.01)

(52) U.S. Cl.
CPC .............. *A61B 5/0816* (2013.01); *A61B 5/01* (2013.01); *A61B 5/682* (2013.01); *A61B 5/7278* (2013.01); *A61B 5/087* (2013.01); *A61B 5/113* (2013.01); *A61B 5/681* (2013.01); *A61B 5/6833* (2013.01); *A61B 2562/0261* (2013.01)

(58) Field of Classification Search
CPC ......... A61B 5/0816; A61B 5/01; A61B 5/682; A61B 5/7278; A61B 5/087; A61B 5/113; A61B 5/681; A61B 5/6833; A61B 2562/0261
USPC ................................................. 600/529–543
See application file for complete search history.

(56) References Cited

U.S. PATENT DOCUMENTS

| | | | | |
|---|---|---|---|---|
| 4,982,735 A * | 1/1991 | Yagata | ................... | A61M 16/00 128/204.21 |
| 6,941,952 B1 * | 9/2005 | Rush, III | .............. | A63B 71/085 128/845 |
| 9,955,918 B2 * | 5/2018 | Paris | ..................... | A61B 5/6803 |
| 10,251,774 B2 * | 4/2019 | Shah | ........................ | A61F 5/566 |
| 10,542,929 B2 * | 1/2020 | Kimmel | .................. | A61B 5/486 |
| 2008/0078392 A1 * | 4/2008 | Pelletier | .............. | A61M 16/024 128/204.23 |
| 2012/0172677 A1 * | 7/2012 | Logan | .................... | A61B 5/082 600/301 |
| 2013/0253286 A1 * | 9/2013 | Fridman | .............. | A61B 5/0402 600/301 |
| 2014/0187875 A1 * | 7/2014 | Paris | .................... | A61B 5/6803 600/301 |

(Continued)

*Primary Examiner* — Navin Natnithithadha
(74) *Attorney, Agent, or Firm* — Kelley Drye & Warren LLP

(57) ABSTRACT

An improved device for monitoring respiration or other vital signs of a user using one or more sensors. The invention may be worn within the mouth of the user to allow more accurate, direct, and fast measurements. The invention may also include a distribution mechanism that may be used to administer a substance such as medication. The substance may be administered in response to data collected by one or more of the sensors in the device and/or in response to data received from another device.

21 Claims, 5 Drawing Sheets

(56) References Cited

U.S. PATENT DOCUMENTS

| | | | |
|---|---|---|---|
| 2014/0350354 A1* | 11/2014 | Stenzler | A61B 5/4818 600/301 |
| 2016/0120462 A1* | 5/2016 | Tunnell | A61B 5/486 600/532 |
| 2016/0242692 A1* | 8/2016 | McAuliffe | A61B 5/228 |
| 2017/0238863 A1* | 8/2017 | Kimmel | A61B 5/7282 |
| 2017/0312117 A1* | 11/2017 | Shah | A61M 16/0069 |
| 2017/0319129 A1* | 11/2017 | Shah | A61M 16/0069 |
| 2018/0000563 A1* | 1/2018 | Shanjani | H04B 5/0056 |
| 2018/0116863 A1* | 5/2018 | Shah | A61B 5/0878 |
| 2018/0242911 A1* | 8/2018 | Paris | A61B 5/6803 |

* cited by examiner

MONITOR OF ORAL RESPIRATION

CROSS-REFERENCE TO RELATED APPLICATIONS

This application claims the benefit of U.S. Provisional Patent Application No. 62/634,775, filed on Feb. 23, 2018. The entire contents of that application are incorporated herein by reference.

FIELD OF THE INVENTION

The invention relates to the field of wearable sensors and, more particularly, to electronic devices which may be used to monitor a wearer's vital signs.

BACKGROUND OF THE INVENTION

Vital signs are measures of the body's most basic functions, and are routinely used to help detect or monitor medical problems. The four primary vital signs monitored by medical professionals and health care providers are body temperature, blood pressure, pulse (heart rate), and respiration rate (rate of breathing). Body temperature can be measured with a thermometer, blood pressure with a blood pressure cuff and stethoscope, heart rate by simply counting the number of pulses in a minute, and respiration rate by simply counting the number of chest movements corresponding to breaths in a minute.

There have been prior attempts to gauge vital signs by wearing electronic devices outfitted with different kinds of sensors on the outside of the body. Such devices take different form factors (e.g., watch-type wristbands, straps, adhesive patches) and range in the kinds and sources of signals they measure, from an EKG that measures heart rate to a pulse oximeter on the finger tip that estimates peripheral blood oxygen saturation as a proxy for respiration rate. While indirect measures of respiration can be useful for gauging stress and fitness level (e.g., https://spire.io), they are not sensitive or accurate enough to depend on to save someone's life in cases such as respiratory depression, which a person might experience during an opioid drug overdose.

Changes in respiration rate can fluctuate rapidly, so a fast, accurate, passive, and objective measure is preferable for critical situations. Of the vital signs that may be measured for a patient in a hospital, however, respiration is the most subjective and indirect of assessments. While existing sensors may be used to monitor heart rate and temperature in an automated manner, monitoring respiration typically requires in-person attention and time intensive measurement by hospital staff. Nurses may count a patient's breaths while looking at their watches and then divide the elapsed time by breath count to assess respiration. This technique is often inaccurate. Also, because the required labor of performing manual measurements can be time consuming and costly, respiration measurements may not be taken as often as they otherwise would, either accidentally or intentionally, potentially leading to decreased quality of care.

Where speed and accuracy are required, direct measures of respiration would be far more reliable and would enable a more rapid and appropriate response to an emergency. In cases where there is not a life-threatening emergency, such as in sleep apnea, measuring breathing in a sensitive, fast, and accurate manner can still lead to more effective interventions and provide longer term health benefits. There is therefore a need for improved devices for monitoring a person's vital signs and methods that overcome some or all of the previously described drawbacks.

SUMMARY OF THE INVENTION

The present invention is directed to an improved device for monitoring vital signs of a user using one or more sensors. The invention may be worn within the mouth of the user or elsewhere in the airway to allow more accurate, direct, and fast measurements. For example, the invention may be integrated in equipment used for intubation, such as endotracheal respiration tubes, oropharyngeal airway respiration tubes, nasopharyngeal airway respiration tubes, and/or an ADC Berman oral airway device.

Monitoring vital signs of a user by collecting data from within the user's mouth and/or one or more other locations in the user's airway provides a number of advantages. For example, measuring respiration within the oral cavity or nose of a user may provide one or more of the following advantages over indirect measures taken outside of the body: (1) it allows faster and more accurate readings of respiration, (2) it allows access to body cavities and mucous membranes for additional sensor-based readings such as temperature, humidity, chemical assays of mucus and saliva, and/or (3) it allows access to mucous membranes for administering a drug in response to changes in vital signs such as respiratory depression.

A device according to the present invention may further include a microcontroller which may be used to control one or more sensors of the device, collect data from the one or more sensors, process data from the one or more sensors, and store data. The present invention may also include a distribution mechanism that may be used to administer a substance to the user. The substance may comprise medication. Also, the substance may be administered in response to data collected by one or more of the sensors in the device and/or in response to data received from another device.

Numerous variations may be practiced in the preferred embodiment.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

The invention may be understood more readily by reference to the following detailed descriptions of preferred embodiments of the invention. However, techniques, systems, and operating structures in accordance with the invention may be embodied in a wide variety of forms and modes, some of which may be quite different from those in the disclosed embodiments. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
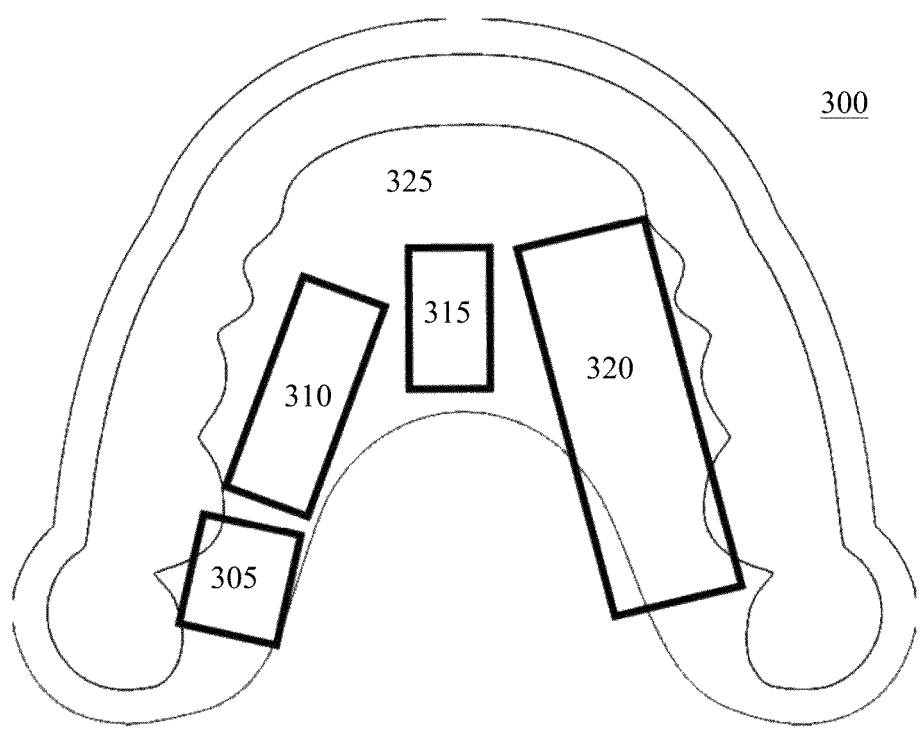
FIG. 1 depicts a schematic of components that may be included in an embodiment of the invention.

FIG. 1 depicts an embodiment of the present invention. The present invention may be an intraoral device, such as a retainer, a mouthpiece, a tooth implant, or a device cemented to a molar, that may include one or more of the following: a microcontroller (e.g., a Nordic nRF51822 ARM Cortex M1 Bluetooth communications SoC (System On a Chip)), a rechargeable battery, a vibration motor, a battery charging circuit, and sensors such as: (1) an integrated barometric air pressure sensor, humidity sensor and air temperature sensor (e.g., a Bosch BME); (2) a thermopile contactless thermometer with secondary device temperature sensor (e.g., Melexis MLX90615); and/or (3) a 3-axis accelerometer (e.g, Kionix KX022). A device according to the present invention may include a subset of one or more of those sensors or may have multiple instances of one or more of each sensor.

During operation, the one or more sensors may be continuously sampled by the microcontroller. Data collected may include data regarding air pressure, changes in pressure over time, humidity, air temperature, skin temperature, changes in skin temperature over time, and/or device temperature. The data collected from the sensors may be filtered and analyzed to find patterns which correspond to a user's respiratory waveform (e.g., a waveform depicting the user's respirator rate) or other vital signs. For example, the device may be used to passively track a user's breathing. Data concerning the user's breathing may be used to monitor a user's respiration and/or respiratory pattern. The user's respiration may output to a computer display as a respiratory wave form, and or may be depicted as the breathing rate of a pair of simulated lungs.

As depicted in FIG. 1, the present invention includes a device (300) in which electronic components may be mounted on a wearable oral platform such as a hard plastic orthodontic retainer (325). The electronic components may include device sensors (305), a microcontroller (310), a battery (315), and a distribution mechanism (320). Device sensors (305), such as one or more temperature sensors, one or more air pressure sensors, and/or one or more humidity sensors, may be positioned to take advantage of the airway's unique characteristics. Also, although FIG. 1 depicts sensors located in one configuration, sensors may be located anywhere on the device.

Figure 4:
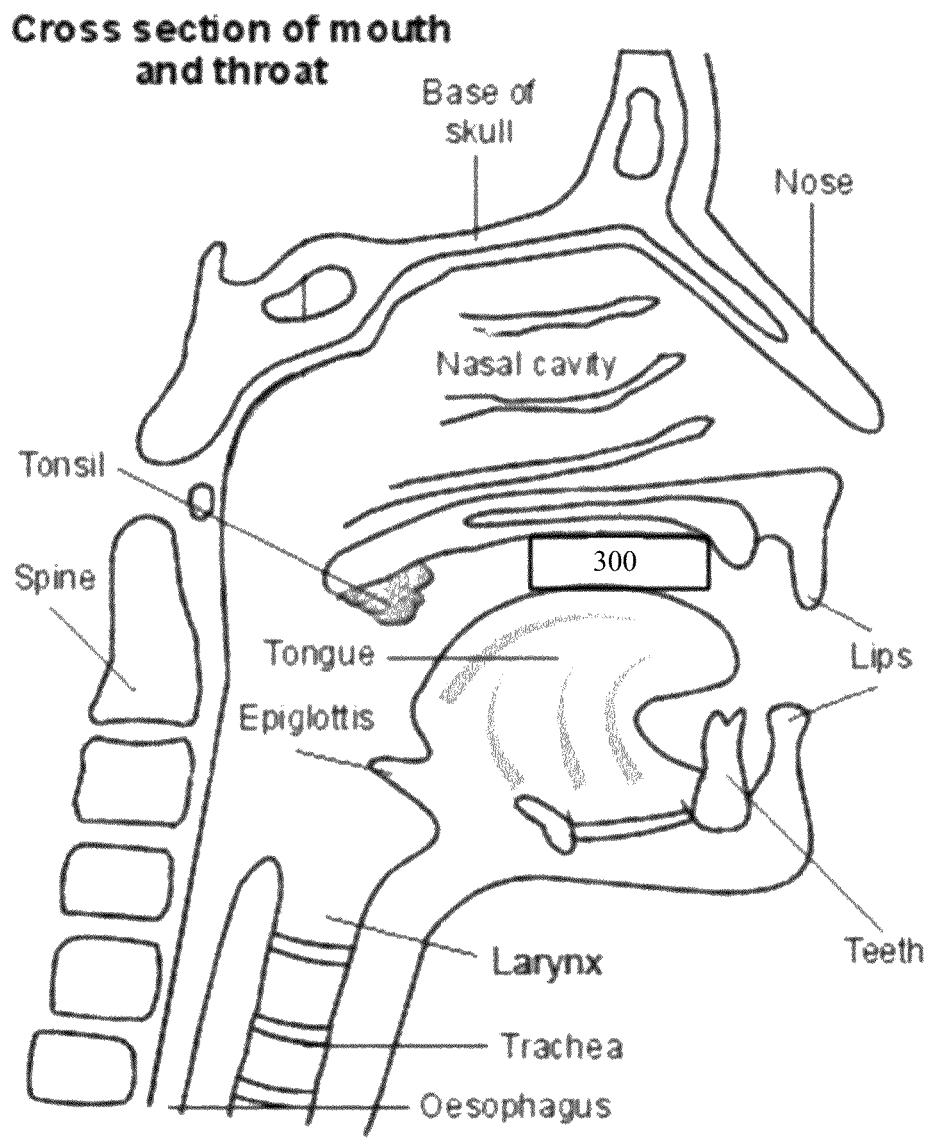
FIG. 4 depicts a cross section of a user's head showing an exemplary position of an embodiment of the present invention.

When device (300) is worn, it may be positioned at the top of the user's mouth as shown in FIG. 4. Temperature sensors such as thermopile sensors—preferably having a field of view directed at a surface of the user's mouth—may be positioned to detect inner-airway skin temperature at the back of the mouth to better determine temperature fluctuations during closed mouth breathing. Other sensors such as air/gas pressure sensors may also be included. Sensors which might be damaged by direct contact with water (e.g., air pressure sensors) may be protected by a waterproof (or water-resistant), air permeable (breathable) barrier made of material such as Tyvek or Gore-Tex, or by a hydrophobic material. Surgical tape may also be used to secure and/or protect an air pressure sensor.

Microcontroller (310), such as a Nordic nRF51822 microcontroller, may be used to run the device software, and/or control communications with computers and smartphones. Communication may be accomplished over a Bluetooth connection by using, for example, a Bluetooth BLE data transmission radio. Other known means of wireless or wired communication with external computational devices and/or computer networks may be used.

Data from one or more sensors may be used to monitor a user's respiration in varying circumstances. For example, when a user's mouth is closed and the user is breathing through the user's nose, air pressure within the mouth may be used to monitor the user's respiration. The nose is a constricted airway, so when inhaling through the nose, air pressure builds in the mouth because the air in the mouth is in fluid communication with the air in the nose. When exhaling through the nose, air pressure drops. One or more air/gas pressure sensors may be used to measure the changes in air pressure to monitor a user's respiration while the user is breathing through their nose.

When a user's mouth is open, because the mouth is a relatively large airway as compared to the nose, the change in air pressure is not as great and may not be as easy to monitor. However, air in inhaled through the mouth is typically not the same temperature as a person's body. So when cool air enters the mouth during inhalation, it passes the back of the throat and cools the skin. When warmer air is exhaled from the lungs, it warms the skin at the back of the throat. So when a user's mouth is open, data from sensors on the device reflecting interior skin temperature (e.g., skin within the user's airway) may be used to measure to monitor the user's respiration.

Further to the discussion above, respiration rate and related respiratory data such as force of respiration, acceleration of respiration, and speed of respiratory action components may be modeled and approximated from device sensor data. For example, a raw time series plot of air pressure and intraoral skin temperature data may present a regular rise and fall of sensor values similar to a sine wave. The raw values collected over multiple breaths can be applied to a polynomial or sinusoidal regression, producing a function which approximates respiration. The period of this function may correspond to the respiratory rate of the individual wearing the device, with the x-axis corresponding to time and the y-axis corresponding to sensor values. Such a regression could be applied separately to temperature and air pressure data, with the regression which most strongly reflects gathered data being prioritized. In such a context, the regression function of air pressure would be expected to perform best when the mouth is closed, and the regression function of intraoral skin temperature would be expected to perform best when the mouth is open. The respiratory rate could also be approximated through peak detection, and time measured between peaks. Peak detection might be accomplished by finding where the first derivative of the function is zero (where acceleration is zero).

In addition to a regression analysis or in the alternative, a simpler filtering method might be used to approximate respiratory rate. Peaks and troughs in sensor value data might be identified and compared to one another. The periods between peaks may be analyzed to determine a consistent pattern of similar periods between peaks. The individual time between peaks as a component of a regular and consistent time between multiple peaks would approximate the user's respiratory rate.

A generalized, user-specific or case-specific neural network model may be generated to analyze sensor data and provide respiration rate and other respiratory information. A training set of data may be generated by collecting device sensor data concurrently with reference data corresponding to respiration. For example, air pressure and intraoral skin temperature data might be collected concurrently with data from a chest belt monitoring respiration by way of measuring the expansion and contraction of the chest as the user's lungs are inflated and deflated. Sensor data from the device might also be collected concurrently with data from a spirometer. Sensor data from the device might also be collected concurrently with video or in-person observation of the chest expanding and contracting. In all cases, data from the device and reference data may be time stamped.

The device and reference data might be used to train a neural network model, such as a multilayer perceptron (MLP), a class of feedforward artificial neural network. A neural network consists of input nodes, output nodes and hidden layers of nodes between inputs and outputs—all connected by weight values. In this case, air pressure and intraoral skin temperature data may be applied to the input nodes of the neural network model, while reference data collected at the same time as the device sensor data may be applied to the output nodes. Additional sensor data, for example, data from an accelerometer and/or a humidity sensor, may also be added as input nodes. The weight values connecting nodes within the network may begin at a standard value. After the model is trained, the weight values may produce an output value from the input values. The model may be subjected to multiple training iterations, often thousands or even millions of iterations. During each training iteration, the weight values may be slightly changed, preferably in a random fashion. The output generated by the new model with changed weight values is compared to the reference output data by applying the reference data to the output nodes. If the output of the new model more closely approximates the training reference data than the old model, the new model (with new weight values) is retained. Otherwise the model reverts to its old state. Over many iterations, the model may become more accurate as the generated output more closely approximates the training reference data from a chest strap, a spirometer, observation and/or other sources. Once the model is trained, device sensor data may be applied to the input nodes and an output may be generated corresponding to respiration rate or other information pertaining to respiration such as acceleration of respiration. Training data may be gathered from a particular user to create a personalized model, or data might be gathered from many people to create a generalized model.

Respiration may also be monitored by comparing changes in data collected from one or more sensors to one or more predetermined values or percentages. For example, the device according to the present invention may include sensors that measure air pressure and skin temperature as described above. Data collected by those sensors, may be used to measure the change in air pressure and/or the change in skin temperature over time. A predetermined change or a predetermined percentage change in the data collected may be used to determine whether the user is inhaling or exhaling. For example, if an air pressure sensor of an intraoral device according to the present invention collects data indicating an increase in air pressure of greater than a certain percentage, such as 15%, the system may consider that change to indicate that the user is inhaling (likely through the user's nose). A corresponding decrease in air pressure—either by a predetermined amount, or a predetermined percentage—may indicate that the user is exhaling. Data collected from one or more temperature sensors may be simultaneously monitored to, for example, confirm that the user is breathing through the user's mouth or nose. For example, a constant temperature or a change in temperature (or percentage change in temperature) below a certain threshold may be used to confirm that the user is breathing through the user's nose.

A change in skin temperature may also be used to determine when a user is inhaling or exhaling. For example, a decrease in skin temperature by a certain amount or by a certain percentage may indicate that the user is inhaling (likely through the user's mouth), whereas an increase in skin temperature may indicate that the user is exhaling. Data collected from one or more air pressure sensors may be simultaneously monitored to, for example, confirm that the user is breathing through the user's mouth or nose. For example, a constant air pressure or a change in air pressure (or percentage change in temperature) below a certain threshold may be used to confirm that the user is breathing through the user's mouth.

Figure 5:
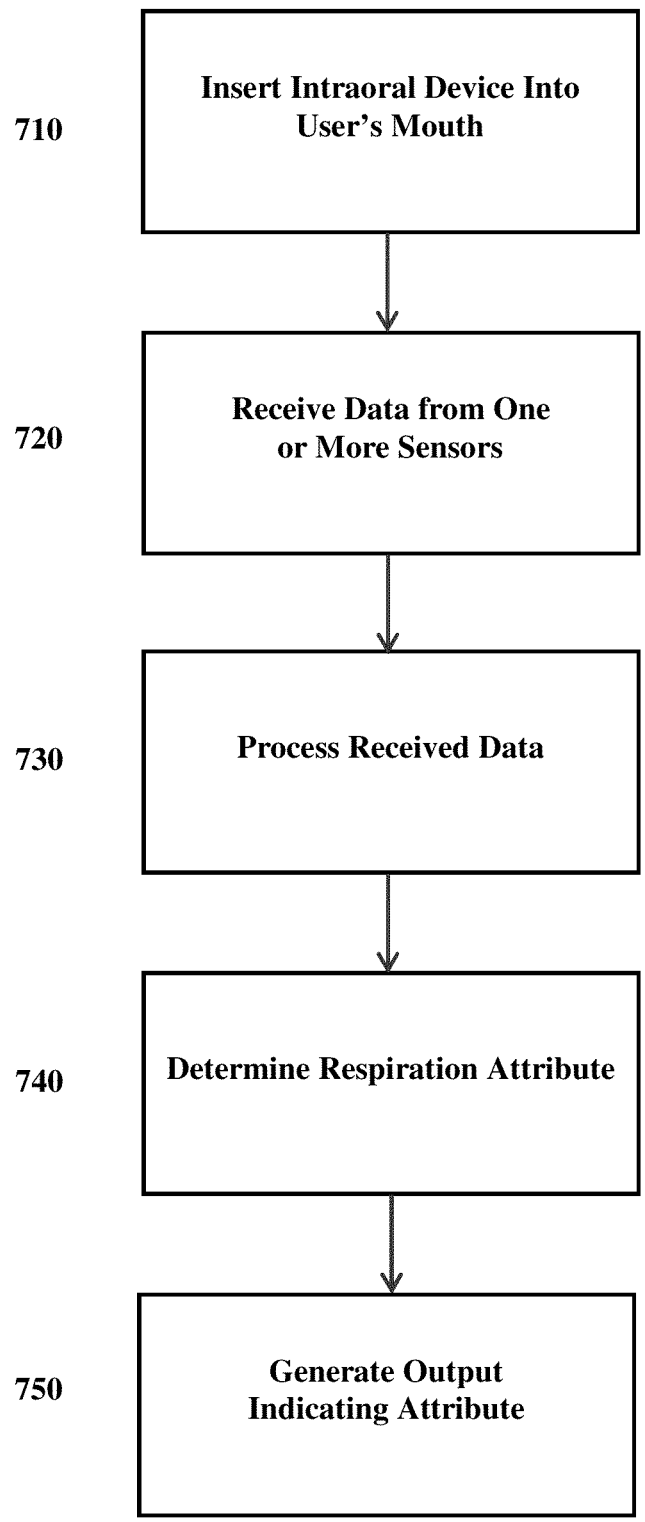
FIG. 5 is a flow chart depicting a method according to an embodiment of the present invention.

An exemplary method is shown in FIG. 5. At Step (710), an intraoral device according to the present invention may be inserted into a user's mouth. As noted above, the intraoral device may be, for example, a retainer, a mouthpiece, a tooth implant, or a device cemented to a molar. The intraoral device may include an air pressure sensor and/or a temperature sensor.

At Step (720), one or more sensors of the intraoral device may be used to measure temperature, air pressure, or one or more other conditions. Data may be collected from each sensor simultaneously, or data may be collected during alternating periods of time from each sensor. For example, a first sensor may collect data for a first predetermined period of time, such as one second. After the predetermined period of time, a second sensor may collect data for a second predetermined period of time, which may or may not be the same as the first predetermined period of time.

At Step (730) one or more processors may be used to process data collected from the sensor or sensors. As described above, the data may be used to measure the change in air pressure and/or the change in skin temperature over time.

At Step (740), a change or percentage change in the data collected may be used to determine a respiration attribute or condition of the user, such as whether the user is inhaling or exhaling and/or the respiratory rate of the user. For example, as noted above, a change in skin temperature during a predetermined period of time may indicate that the user is breathing through the user's mouth. The one or more processors may measure the maximum and minimum temperature values (or approximate maximum and minimum temperature values) over a predetermined period of time, calculate the difference or percentage difference between the maximum and minimum temperature values, and compare the difference or percentage difference to a threshold value or threshold percentage to determine whether the change in temperature indicates that the user is breathing through the user's mouth. Alternatively or in addition, the one or more processors may measure the maximum and minimum air pressure values (or approximate maximum and minimum air pressure values) over a predetermined period of time, calculate the difference or percentage difference between the maximum and minimum air pressure values, and compare the difference or percentage difference to a threshold value or threshold percentage to determine whether the change in air pressure indicates that the user is breathing through the user's nose.

At Step (750), the one or more processors may generate an output indicating the respiration attribute or condition of the user. The output may indicate, for example, whether the user is breathing through the user's nose or mouth. In addition or in the alternative, the output may indicate the respiratory rate of the user.

Referring again to FIG. 1, a distribution mechanism (320) may be controlled in such a way as to cause a substance to be extruded into the mouth at a desired point in time. Distribution mechanism (320) may function in one of a number of ways, including: (1) an electric motor pump may eject a substance from a reservoir; (2) an electric motor linear actuator may move a plunger which ejects a substance from a reservoir; (3) an electric motor may trigger a tightened or wound spring which ejects a substance from a reservoir; or (4) a chemical reaction may produce an expanding gas which pushes a flexible membrane inside a drug administration cartridge such that a substance is extruded. The substance ejected by distribution mechanism (320) may be medication, such as Naloxone.

Figure 2:
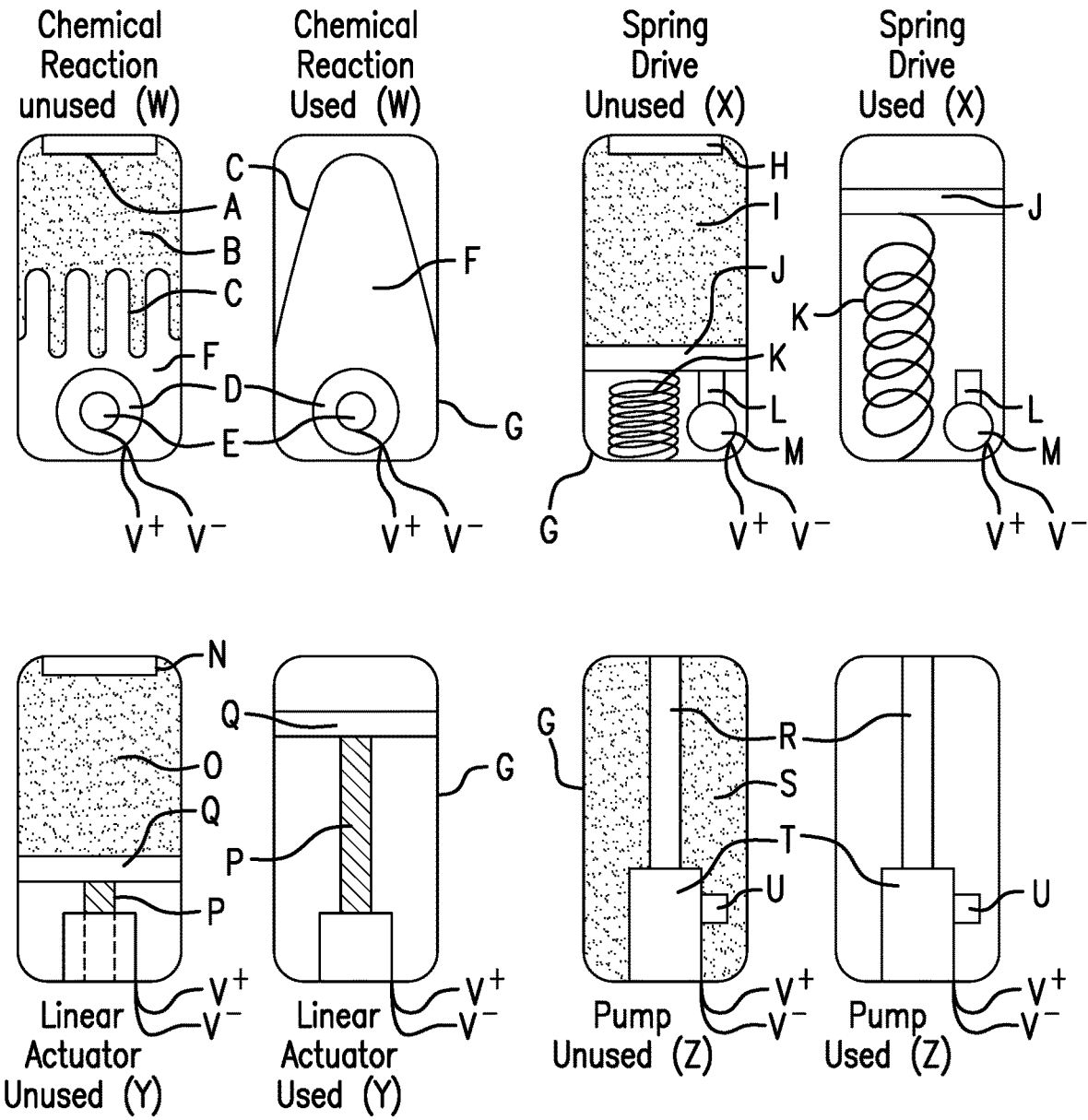
FIG. 2 depicts exemplary substance distribution cartridges.

FIG. 2 depicts exemplary cartridges that may be incorporated within distribution mechanism (320), and may be used to hold the substance until the substance is ejected. The cartridge may be composed of an outer casing (G) which may be a hard or soft plastic. The casing may be designed such that the substance within the casing is under greater pressure than the area exterior to the casing. The cartridge may contain a sealed reservoir (B, I, O, S) of the substance to be distributed. The cartridge may contain a temporary seal (A, H, N) which will allows the substance in question to eject into the surrounding area when sufficient pressure is generated inside the cartridge.

The mechanism by which the cartridge is actuated may take several forms, such as pressure generated by a chemical reaction (W), pressure generated by the release of a spring or similar implement under tension (X), pressure generated by an electric motor linear actuator (Y) or the operation of an electric motor pump (Z). The chemical reaction may be driven by the combination of two non-toxic substances, for example sodium bicarbonate (baking soda) and acetic acid (vinegar). Acetic acid may be stored in a reservoir (F), separated from the substance to be administered by a flexible membrane of plastic or similar material (C). Sodium bicarbonate may be stored in a sealed container (D) within the acetic acid reservoir. The seal of this sodium bicarbonate container may be attached to an electric motor vibration generator (E). At a desired moment in time, the electric vibration motor may be turned on, and the kinetic energy generated from the motor may breach a seal of the container holding the sodium bicarbonate and allow the sodium bicarbonate to mix with the acetic acid. The resulting reaction may produce carbon dioxide, which generates pressure against the membrane (C), separating the acetic acid reservoir from the substance to be administered reservoir. The generated pressure may breach the temporary seal (A), ejecting the substance to be administered out of the cartridge.

Cartridge mechanism (X) containing a spring or similar implement (K) may also contain a mechanical trigger (L) attached to an electric vibration motor (M) or other source of kinetic energy. The mechanism (X) may also contain a hard barrier (J) separating the spring and vibration motor from a reservoir (I) of the substance to be administered. At a desired moment the vibration motor (M) may be turned on, and the kinetic energy produced thereby may actuate trigger (L), which releases spring (K). The spring may drive hard barrier (J) against reservoir (I). The pressure generated inside the reservoir by the spring may breach a temporary seal (H), allowing the substance to be expelled from the cartridge.

Another embodiment of the cartridge (Y) may contain an electric motor linear actuator (P). When the linear actuator is turned on, it may drive a hard barrier (Q) against a reservoir of the substance to be administered (O), creating pressure within the reservoir, which may breach a temporary seal (N), ejecting the substance to be administered out of the cartridge. Another embodiment of the cartridge (Z) may contain an electric motor pump. The pump will have an input outlet (U) in a reservoir of the substance to be administered (S) and an output outlet (R) exposed to the exterior of the cartridge. When the pump is activated, it may draw the substance to be administered from the reservoir and expel it outside the cartridge.

Figure 3:
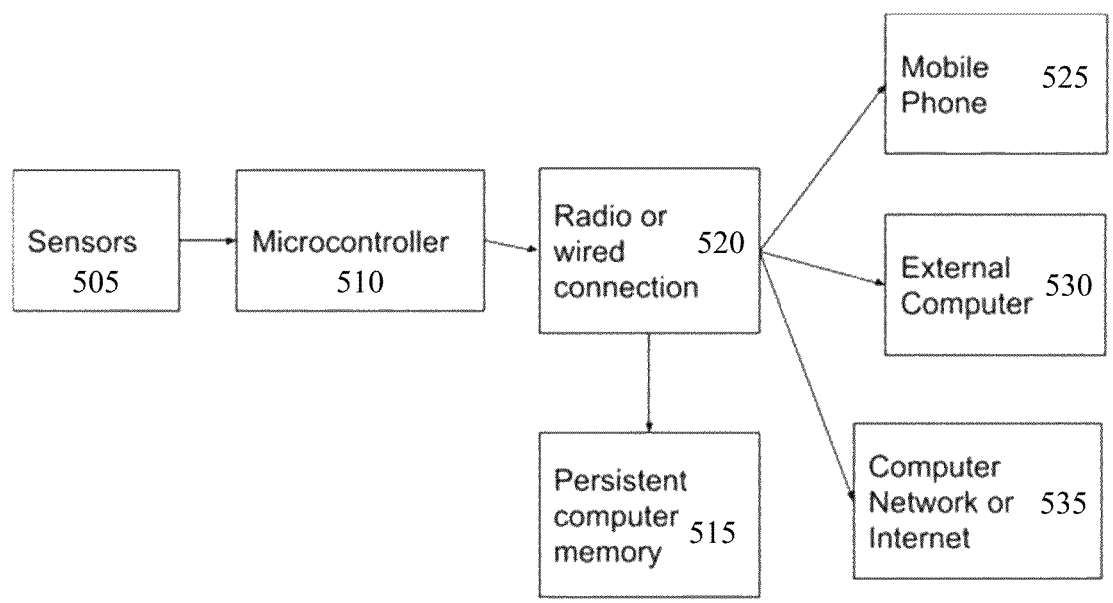
FIG. 3 depicts a schematic of components according to the present invention.

Referring to FIG. 3, a schematic according to an exemplary embodiment of the present invention is shown. Information may be gathered from device sensors (505). The information may be sent to device microcontroller (510), which may be, for example, a Nordic nRF51822. The information received by device microcontroller (510) may be processed for transmission or storage.

Information and/or machine executable code used to operate the device and/or analyze data collected by one or more sensors may also be stored in memory (515), for example NAND Flash, FRAM or EEPROM. Device microcontroller (510) may be used to execute software (e.g., machine executable code) to receive data from one or more sensors, analyze sensor data, which might include data concerning respiration, heart rate and/or other physiological phenomena, and/or generate an output. In addition or in the alternative, data received from the sensors or an analysis of the data performed by device microcontroller (510) may be transmitted from the device to one or more other devices—such as a mobile phone (525), external computer (530) or device connected to a computer network (535)—by one of a number of known means of transmission, such as a wired connection or radio transmitter (520).

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A system for monitoring respiration of a user, comprising:
an intraoral device having an air pressure sensor and a temperature sensor;
a memory having a machine-readable medium comprising machine executable code; and
one or more processors coupled to the memory, said one or more processors configured to execute the machine executable code, wherein the machine executable code is capable of causing the one or more processors to:
receive a set of data comprising data output from the air pressure sensor and data output from the temperature sensor;
process the received data to identify a respiratory attribute of the user based on whether the received data indicates a change in pressure that exceeds a first predetermined percentage change or a change in temperature that exceeds a second predetermined percentage change; and
generate an output indicating the attribute,
wherein the machine executable code is capable of causing the one or more processors to process the received data using a machine learning algorithm.

2. The system of claim 1, wherein the respiratory attribute identifies whether the user is inhaling or exhaling.

3. The system of claim 1, wherein the machine learning algorithm is a neural network.

4. The system of claim 3, wherein the temperature sensor is a thermopile having a field of view directed at a surface of the user's mouth.

5. The system of claim 1, wherein the temperature sensor is a thermopile having a field of view directed at a surface of the user's mouth.

6. The system of claim 1, wherein the respiratory attribute comprises the user's respiratory rate.

7. The system of claim 1, wherein the respiratory attribute comprises a change in the user's respiratory rate.

8. The system of claim 1, wherein the respiratory attribute comprises a waveform depicting the user's respiratory rate.

9. The system of claim 1, wherein the pressure sensor is at least partially covered by a water-resistant, breathable membrane.

10. The system of claim 9, wherein the membrane comprises Tyvek.

11. The system of claim 9, wherein the membrane comprises Gore-Tex.

12. The system of claim 11, wherein the intraoral device is a retainer.

13. The system of claim 11, wherein the intraoral device is a mouthpiece.

14. The system of claim 11, wherein the intraoral device is a tooth implant.

15. The system of claim 11, wherein the intraoral device is cemented to a molar of the user.

16. The system of claim 1, wherein the temperature sensor is a thermopile.

17. The system of claim 16, wherein the thermopile has a field of view directed at a surface of the user's air pathway.

18. A system for monitoring respiration of a user, comprising:
an intraoral device having a pressure sensor and a temperature sensor;
a memory having a machine-readable medium comprising machine executable code; and
one or more processors coupled to the memory, said one or more processors configured to execute the machine executable code, wherein the machine executable code is capable of causing the one or more processors to:
receive data comprising data output from the pressure sensor and data output from the temperature sensor;
determine whether the received data indicates a change in pressure that exceeds a first predetermined percentage change;
determine whether the received data indicates a change in temperature that exceeds a second predetermined percentage change; and
generate an output indicating whether the user is exhaling or inhaling based on the change in pressure exceeding a first predetermined percentage change or the change in temperature exceeding a second predetermined percentage change.

19. The system of claim 18, wherein the pressure sensor is at least partially covered by a water-resistant, breathable membrane.

20. The system of claim 19, wherein the membrane comprises Tyvek.

21. The system of claim 19, wherein the membrane comprises Gore-Tex.

* * * * *